United States Patent [19]

Pohjala et al.

[11] Patent Number: 5,776,499
[45] Date of Patent: *Jul. 7, 1998

[54] PROCESS FOR PREPARING A CLODRONATE PREPARATION

[75] Inventors: Esko Pohjala, Tampere; Heikki Nupponen, Kangasala; Kari Lehmussaari, Tampere, all of Finland

[73] Assignee: Leiras Oy, Turku, Finland

[*] Notice: The term of this patent shall not extend beyond the expiration date of Pat. No. 5,525,354.

[21] Appl. No.: 646,359

[22] PCT Filed: Nov. 11, 1994

[86] PCT No.: PCT/FI94/00509

§ 371 Date: Aug. 6, 1996

§ 102(e) Date: Aug. 6, 1996

[87] PCT Pub. No.: WO95/13054

PCT Pub. Date: May 18, 1995

[30] Foreign Application Priority Data

Nov. 11, 1993 [FR] France .......................... 93509

[51] Int. Cl.$^6$ .......................................... A01K 9/14
[52] U.S. Cl. ............................... 424/489; 424/51
[58] Field of Search .................................. 424/451, 489

[56] References Cited

U.S. PATENT DOCUMENTS 5,525,354  6/1996  Posti .......................... 424/451

FOREIGN PATENT DOCUMENTS

| 0 275 468 B1 | 7/1988 | European Pat. Off. . |
| 0 625 355 B1 | 11/1994 | European Pat. Off. . |
| WO 93/21907 | 11/1993 | WIPO . |

*Primary Examiner*—Thurman K Page
*Assistant Examiner*—D. Faulkner

[57] ABSTRACT

The object of the invention is a process for preparing a clodronate preparation. The process is characterized in that clodronate is crystallized as disodium clodronate tetrahydrate from an aqueous solution of disodium clodronate; the resulting disodium clodronate tetrahydrate is dry granulated by compressing in such a way that the crystal structure of the disodium clodronate tetrahydrate is preserved and by crumbling and screening the mass to granules of a sutiable size, the dry granulated disodium clodronate tetrahydrate is optionally mixed with suitable excipients, such as filling agents and gliding agents and, if necessary, disintegrants.

18 Claims, No Drawings

PROCESS FOR PREPARING A CLODRONATE PREPARATION

This application is a continuation of PCT/FI94/00509 filed Nov. 11, 1994.

The object of the present invention is a process for preparing a clodronate preparation by dry granulation, where the crystalline phase of the clodronate raw material used is the stable and easy-to-handle tetrahydrate of the clodronic acid disodium salt ($CH_2Cl_2O_6P_2Na_2 \cdot 4H_2O$), with a definite crystal form.

Clodronate or the disodium salt of (dichloromethylene) bisphosphonic acid, tetrahydrate, is useful for instance in the treatment and prophylaxis of disorders of the calcium metabolism, such as bone resorption, hypercalcaemia and osteoporosis. Based on its ability to form a strong complex with a $Ca^{2+}$-ion, clodronate removes excessive calcium from the circulation, prevents calcium phosphate from dissolving from the bone and/or acts via cell-mediated mechanisms. However, it is necessary to administer clodronate in relatively large doses for a prolonged time. A problem with clodronate preparations has therefore been how to achieve a sufficiently high amount and concentration of the active agent in a capsule or tablet, without having to use capsule or tablet sizes which are unpleasantly large for the patient.

Due to the properties of clodronate, it has in practice turned out that untreated clodronate raw material is difficult to mix to a homogenous mixture with other excipients and active agents present in the preparation.

Processes previously used for the preparation of clodronate preparations have been disclosed for instance in the publication EP 275 468, which relates to a process for preparing a clodronate preparation by a wet granulation process. In the process the raw materials are mixed dry, a granulating liquid is added, the mixture is wet granulated and the granulate is dried.

Due to the properties of clodronate, the clodronate powder thus obtained is, however, inaccurate as regards its composition and obviously difficult to handle (sticky, very poor flow properties). It is thus extremely difficult in practice to mix it with other substances used in the preparation, as well as to further process it, wherefore for instance a relatively large amount of gliding agents is needed. From the unhomogenous raw powder an unhomogenous and poorly flowing product mass is then obtained, which affects also the accuracy of dosing of the final medicament.

In the absorption of clodronate, as well as of other bisphosphonates, phosphonates, great individual and diet-related differences have been observed, wherefore the homogenity of the drug and the pharmaceutical preparation is essential for the determination of a suitable dose and for the follow-up of the treatment.

The bulk volume of the clodronate raw material generally varies a great deal between different batches of preparation, due to the difficultly controlled crystallization process in the preparation of the raw material, where the four crystal waters must have time to take their positions in the crystal lattice in order to obtain a uniform and non-caking composition but where, on the other hand, a too slow crystallization leads to an unsuitably large crystal volume. In a wet granulation process this has the effect that the amount of granulating liquid has to be varied from one granulation batch to the next, depending on the quality of the raw clodronate, in order to obtain, as the end product, granules with the same bulk volume. As stated above, the wet granulation process is thus an extremely difficult and laborious process and the final result is often, however, unforeseeably inaccurate. The wet granulation process is always connected with time-consuming and expensive drying of the granules. In addition to the step of manufacturing the raw material, a second balancing regarding the four necessary crystal waters is required in the drying stage of the wet granulation process.

According to the invention it has now surprisingly been discovered that by crystallizing clodronate specifically in the form of stable and non-caking and non-sticky disodium clodronate tetrahydrate, having a predetermined crystal structure and size and thus predetermined properties, and by dry granulating under controlled conditions in such a way that the crystal structure of disodium clodronate tetrahydrate is preserved, the previous problems in the handling of clodronate, as well as the cumbersome wet granulation process which is inaccurate as regards the end product, can be avoided. Especially the four crystal waters of disodium clodronate need to be adjusted correctly only once when this is done already during the preparation of the raw material. In the dry granulation process there is no need for readjustment of the same as in the wet granulation process. Possible differences between batches of raw material, even minor differences in the bulk volume, are evened, provided that the clodronate is composed of crystallized, stable disodium clodronate tetrahydrate, which is suitable for dry granulation. The result is ready-to-use granules of uniform quality from batch to batch, which granules are easily flowing and thus are well mixed with excipients to form a homogenous formulation mass.

Due to the good handling characteristics of granules obtained from the dry granulation process as such but especially when easily filtered, stable, non-caking and non-sticky disodium clodronate tetrahydrate is used, there is not necessarily a need for excipients at all or they are needed in considerably smaller amounts than in the previous methods. Thus the proportion of the active agent in the preparation may be kept higher and also exactly at the desired level.

Dry granulation is thus an effective way to minimize the bulk volume of the clodronate raw material. This is particularly of advantage when clodronate is administered in capsule form, whereby the size of the capsule may be chosen as small as possible.

The object of the present invention is thus a process for preparing a clodronate preparation, which process comprises the following steps:

- clodronate is crystallized as disodium clodronate tetrahydrate from an aqueous solution of disodium clodronate,
- the resulting disodium clodronate tetrahydrate is dry granulated by compressing in such a way that the crystal structure of the disodium clodronate tetrahydrate is preserved, and thereafter by crumbling and screening the mass to granules of a suitable size,
- the dry granulated disodium clodronate tetrahydrate is optionally mixed with suitable excipients, such as filling agents and gliding agents and, if necessary, disintegrants.

In the process according to the invention, clodronate is first crystallized as disodium clodronate tetrahydrate from an aqueous solution of disodium clodronate. Due to the choice of crystallization conditions, stable disodium clodronate with four crystal waters is obtained, either as easily processable flakes or needles, or as a fine crystalline powder with good flowing properties. In both cases the composition of the crystal phase is the same ($CH_2Cl_2O_6P_2Na_2 \cdot 4H_2O$), the crystal form being triclinic and centrosymmetric (AR P1; a=5.911, b=9.190, c=11.284, $\alpha$=89.39, $\beta$=87.36, $\gamma$=88.57, V=612.1, Z=2). One of the four crystal waters is uncoordinated. One of the sodium atoms is coordinated with one chlorine atom. The structure is composed of four-chain bundles of infinite length which are parallel with the a axis and which are connected to each other with hydrogen bridges.

Crystallization may be carried out by adding, in a controlled manner, to an aqueous solution of disodium clodronate an organic solvent which is fully or partly water-soluble but in which disodium clodronate is poorly soluble, and by gradually lowering the temperature while stirring, whereby the disodium clodronate crystallizes as the tetrahydrate. As water-soluble organic solvents, for example, a water-soluble lower alcohol, such as methanol or ethanol, n-propanol, isopropanol, t-butanol, glycol, glycol ethers, tetrahydrofuran, dioxane, acetone, especially ethanol, methanol, monomethyl and ethyl ethers of glycol, tetrahydrofuran, dioxane or acetone, come into question, and ethanol is especially preferred. As a partly water-soluble organic solvent, for example, methylene chloride, chloroform, methyl ethyl ketone, ethyl acetate, butanol, or a mixture of these and completely water-soluble solvents may be used. The starting temperature is higher than room temperature, e.g. 30°–120° C., preferably 60°–100° C., especially 70°–90° C. and most preferably about 80° C. The rate and manner of adding the solvent are to be such that clodronate does not precipitate prematurely or untimely without its crystal water molecules. After the addition the temperature is lowered. The final temperature is 0°–20° C., preferably about 15° C., to which it has been lowered from the starting temperature of 80° C. Temperature may be lowered continuously or stepwise, e.g. by keeping the temperature for a while at about 40° C.

By letting the crystallization take place at an appropriately slow rate as described above, disodium clodronate tetrahydrate is obtained as easily processable fine flakes or needles. The size of the crystals can be adjusted by changing the rate of addition of the organic solvent component and/or the rate of lowering the temperature.

Crystallization may also be carried out by evaporating an aqueous solution of disodium clodronate slowly so that the proportion of water is reduced, in the presence or absence of a water-soluble or partly water-soluble organic solvent, such as mentioned above, and also in the presence of an organic solvent which is poorly soluble in water, in a two-phase system at a temperature of at least about 20° C. but no more than about 100° C., preferably 40°–70° C., while the solution is stirred. If desired, the evaporation may be performed under reduced pressure, whereby the temperature may correspondingly be lower. As a water-soluble organic solvent, for example, a water-soluble lower alcohol, such as ethanol, n-propanol, isopropanol, t-butanol, glycol or glycol ether may be used. As an organic solvent which is poorly or partly water-soluble, for example methylene chloride, chloroform, methyl ethyl ketone, ethyl acetate, butanols, such as 1- and isobutanol, or a mixture of these and those mentioned above come into question, especially methylene chloride, chloroform, 1-butanol, glycol or a monomethyl or monoethyl ether of glycol.

Possible residues of organic solvent may be removed e.g. by washing with ethanol and drying at a temperature, at which the crystalline tetrahydrate does not yet liberate its one crystal water which is most easily released (<50° C.). By crystallizing this way, disodium clodronate tetrahydrate is obtained as a fine crystalline powder with good handling properties.

It is advantageous to use disodium clodronate with four crystal waters as the raw material of a clodronate preparation, which crystal form obtained in the very manner as described above, as a flake, needle and powder, is stable and easy to handle. However, if the equilibrium is disturbed for example by removing or adding crystal waters, i.e. by heating or moistening, the drug raw material becomes sticky or cakes and is thus difficult to handle. Because the first of the four crystal waters is split off relatively easily and rapidly at a temperature of >50° C., it is of vital importance to keep the conditions in the different stages of the manufacturing process of the pharmaceutical preparation such that the tetrahydrate structure is preserved.

Disodium clodronate tetrahydrate, which has been crystallized as described above, may be characterized by powder X-ray diffraction and single crystal X-ray diffraction. The crystal structures measured fully correspond to the published one (Nardelli and Pelizzi, Inorg. Chim. Acta 80 (1983) 289), and thus the structure of the clodronate used in the dry granulation of the invention and of the clodronate crystallized for this purpose according to the invention is correct.

According to our invention it has been found that if the disodium clodronate crystallized as described above is dry granulated under controlled conditions, the structure of disodium clodronate tetrahydrate is preserved and dense, easy-to-handle granules of uniform quality are formed.

According to our invention the granulation is performed as a dry granulation whereby disodium clodronate tetrahydrate is compressed, preferably between rollers, to a thin sheet or mass which is further crumbled and screened to granules of a suitable size. The dry granulation is performed under such temperature and pressure conditions that the crystal structure of the disodium clodronate tetrahydrate is preserved. When the dry granulation is carried out with a roller compactor, the compression pressure is 30–90 bar, preferably 40–75 bar and most preferably about 50–65 bar. The speed of the rollers during compression is 8–16, preferably 8 rpm. Compression is performed at a temperature, which is close to room temperature, however, not higher than about 40°–50° C., preferably at 20°–30° C.

The granules obtained by dry granulation can, if desired, be mixed with suitable excipients, such as filling agents and gliding agents/lubricants and, if necessary, disintegrants. According to the invention, the amount of excipients can be kept low, due to the good handling characteristics of the clodronate granule powder obtained from the dry granulation process.

The use of different excipients in the manufacture of a clodronate preparation is as such known, e.g. DE 2731366, DE 2813121, DE 3500670, EP 336851, U.S. Pat. No. 3,683,080, U.S. Pat. No. 4,234,645. Neither in the manufacture of clodronate preparations nor in the manufacture of other known bisphosphonate preparations has attention previously been paid to the possible role of the crystal waters.

The excipients optionally used in preparations of solid clodronate and mixtures thereof are such that do not bind or release water, in order not to disturb its tetrahydrate structure.

The filling agents (weight balancing agents) to be used may be for example lactose, especially a-lactose monohydrate, microcrystalline cellulose, starch or its derivatives, mannitol, glucose, saccharose, or a mixture of two or more filling agents. A preferred filling agent according to the invention is α-lactose monohydrate, which is used in an amount necessary to adjust the amount of disodium clodronate in the preparation to the desired level. The amount of filling agent is thus about 0–20% by weight, usually about 2–12% by weight, based on the weight of the final preparation.

If necessary, other excipients can also be used, for example flavouring and sweetening agents, such as natural or artificial flavourings and sweeteners, in the amounts needed.

As gliding agents the conventional gliding agents and lubricants known in the art can be used, such as stearic acid or its salts (Mg—, Ca—), talc, starch, colloidal silica or a mixture of two more gliding agents, preferably stearates and/or talc. The amount of gliding agent can and should be kept low, as for example the optional calcium or magnesium containing agents in the preparation bind clodronate by forming a complex therewith, whereby the absorption of the drug is decreased. By using the process according to the invention, the amount of gliding agents can be substantially lowered or its use can even be totally abandoned, whereby the amount of the active agent in the preparation can be kept high and its absorption in the organism does not decrease. Thus the amount of gliding agent can be for example 0–10% by weight, especially 2–6% by weight, based on the weight of the final preparation.

If desired, also disintegrants can be added to the preparation. These are disintegrants generally known in the art, such as for example microcrystalline cellulose, cross-linked sodium carboxymethylcellulose, starch or its derivative, croscarmellose, crospovidone, or mixtures of two or more disintegrants. In the process according to the invention disintegrants may be used for example about 0–3% by weight, especially about 0.5–1% by weight, based on the weight of the final preparation.

By using excipients one can also regulate, if desired, whether a preparation is to decompose in the stomach or only later in the gastrointestinal tract, and also the dissolving rate. Thus the preparation can be coated with as such known film forming agents, which dissolve at the desired pH, such as for example with shellac, cellulose acetate phthalate, hydroxypropyl methylcellulose acetate succinate, hydroxypropyl methylcellulose phthalate, polyvinyl acetate phthalate, cellulose acetate trimellitate or various acryl and methacryl acid derivatives. Film forming agents are known to a person skilled in the art and are commercially available.

The obtained mixture is suitable for administration as a number of different formulations formed from crystal phase clodronate. Thus it can for example be filled in capsules, compressed into tablets or used as granules or a powder according to methods generally known in the art, and further coated, if desired. Especially preferred are capsules and tablets, the size of which can be kept small due to the methods of the invention.

A drug delivery form prepared by the process according to the invention preferably comprises 60–80% by weight of anhydrous disodium clodronate. Preferably it contains 65–75% by weight of anhydrous disodium clodronate (corresponds to about 81–94% of the tetrahydrate form), about 2–12% by weight of a filler, for example lactose, about 2–6% by weight of a gliding agent, for example talc or calcium stearate, and about 0–1%, especially 0.5–1% by weight of a disintegrant, based on the weight of the final preparation.

Representative compositions prepared according to the invention are (% by weight):

|  | % | % | % | % | % |
|---|---|---|---|---|---|
| Anhydrous clodronate | 60 | 65 | 77.2 | 78.4 | 80 |
| Crystal water | 15 | 16.2 | 19.3 | 19.6 | 20 |
| other altogether | 25 | 18.8 | 3.5 | 2 | 0 |
| whereof |  |  |  |  |  |
| Filling agent | 18 | 15 | 2 | 2 | 0 |
| Gliding agent | 4 | 2.8 | 1 | 0 | 0 |
| Disintegrant | 3 | 1 | 0.5 | 0 | 0 |
| Total | 100 | 100 | 100 | 100 | 100 |

The following examples illustrate the invention without limiting the same.

EXAMPLE 1

200 kg of raw clodronate is dissolved in 600 kg of water by heating to 70°–80° C. The pH is adjusted to 3.1 with 1-N hydrochloric acid. 320 kg of ethanol is poured into the solution during 30–40 minutes. The mixture is cooled using circulating water cooling to 35°–45° C. and by cold sol cooling to 10°–15° C. The crystal mass is centrifuged and washed with 10% water-ethanol mixture. The spin-dry product is wet-screened and dried at 30° C. The dried product is mixed, screened and bottled. The yield is 190 kg of disodium clodronate tetrahydrate with a bulk density of 0.25–0.45 g/ml.

The resulting disodium clodronate tetrahydrate was dry granulated by compressing in a roller compactor under a pressure of about 60 bar at room temperature (20°–25° C.) until a suitable bulk density was achieved. The desired bulk density was typically obtained with a granule size over 0.5 mm.

Capsules were prepared with the following composition per capsule:

| Disodium clodronate (calculated as anhydrous) | 400.00 mg |
|---|---|
| Talc | 22.80 mg |
| Calcium stearate | 2.85 mg |
| Anhydrous colloidal silica | 2.85 mg |
| Lactose ad 570.0 mg | 41.50 mg |

The disodium clodronate concentration (as anhydrous) of the composition is thus 70.2% by weight. Granules of dry granulated disodium clodronate tetrahydrate were mixed with calcium stearate, talc, anhydrous silica and lactose The mixture was filled into capsules (size no. 1).

EXAMPLE 2

Disodium clodronate tetrahydrate was dry granulated as described above. Capsules were prepared with the following composition per capsule:

| Anhydrous disodium clodronate | 400.00 mg |
|---|---|
| Lactose ad 570.00 mg | 70.00 mg |

Dry granulated disodium clodronate tetrahydrate and lactose were mixed and the mixture was filled in capsules no. 1.

EXAMPLE 3

Disodium clodronate tetrahydrate was dry granulated as described above. Capsules were prepared with the following composition per capsule:

| | |
|---|---|
| Anhydrous disodium clodronate | 400.00 mg |
| Talc | 22.80 mg |
| Anhydrous colloidal silica | 2.85 mg |
| Lactose ad 570.00 mg | 45.15 mg |

Dry granulated disodium clodronate tetrahydrate, talc, anhydrous silica and lactose were mixed and the mixture was filled into capsules no. 1.

EXAMPLE 4

Disodium clodronate tetrahydrate was dry granulated as described above. Tablets were prepared with the following composition per tablet:

| | |
|---|---|
| Anhydrous disodium clodronate tetrahydrate | 400.00 mg |
| Sodium croscarmellose | 10.00 mg |
| Anhydrous silica | 10.00 mg |
| Magnesium stearate | 5.20 mg |
| Microcrystalline cellulose ad 650 mg | 124.80 mg |

Dry granulated disodium clodronate tetrahydrate, sodium croscarmellose, anhydrous silica and microcrystalline cellulose were mixed into a homogenous mixture. Thereafter magnesium stearate was added to the mixture and stirred. The obtained powder mixture was tabletted using punches of a suitable size, for example round, concave punches with a diameter of 12 mm, to a suitable strength, for example to 7–9 kg.

EXAMPLE 5

Disodium clodronate tetrahydrate was dry granulated as described above. Dosage powders were prepared to be taken as such or to be mixed with water. The composition of the powder per sachet was as follows:

| | |
|---|---|
| Anhydrous disodium clodronate tetrahydrate | 400.00 mg |
| Aspartame | 25.00 mg |
| Flavouring: e.g. lemon | 31.25 mg |
| Magnesium stearate | 3.75 mg |
| Mannitol ad 625 mg | 65.00 mg |

Dry granulated disodium clodronate tetrahydrate, aspartame, flavouring and mannitol were mixed into a homogenous mixture. Then magnesium stearate was added and mixed. The powder mixture was filled into sachets of a suitable size.

EXAMPLE 6

Coated granules:

Disodium clodronate tetrahydrate was dry granulated as described above. The granules were coated with an enteric film in an air suspension apparatus. The composition of the coating:

| | |
|---|---|
| Methyl hydroxypropyl cellulose phthalate | 8.3% |
| Diethyl phthalate | 0.8% |
| Ethanol (96%) | 72% |
| Purified water | 18.9% |

The coated granules may be filled into capsule shells or suitable sachets.

We claim:

1. A process for preparing a clodronate preparation comprising the following steps: clodronate is crystallized as disodium clodronate tetrahydrate from an aqueous solution of disodium clodronate, the disodium clodronate tetrahydrate is dry granulated by compressing in such a way that the crystal structure of the disodium clodronate tetrahydrate is preserved and by crumbling and screening the mass to granules of a suitable size.

2. The process according to claim 1 wherein the disodium clodronate tetrahydrate is crystallized from an aqueous solution of disodium clodronate by adding to the aqueous solution of disodium clodronate a fully or partly water-soluble organic solvent, in which disodium clodronate is poorly soluble, and by gradually lowering the starting temperature which is higher than room temperature.

3. The process according to claim 2 wherein the starting temperature is between 30°–120° C. which is gradually lowered to about 0°–20° C.

4. The process according to claim 3 wherein the starting temperature is between 70°–90° C. and is gradually lowered to about 15° C.

5. The process according to claim 1 wherein the disodium clodronate tetrahydrate is crystallized by evaporating an aqueous solution of disodium clodronate in the presence or absence of a water-soluble or partly water-soluble organic solvent and also in the presence of an organic solvent which is poorly soluble in water, in a two-phase system.

6. The process according to claim 5 wherein the crystallization is performed at a temperature of at least 20° C. and at most 100° C.

7. The process according to claim 2 wherein the water-soluble organic solvent is selected from the group consisting of ethanol, methanol, glycol, monomethyl or monoethyl ether of glycol, acetone, dioxane or tetrahydrofuran, especially ethanol, and the organic solvent is selected from the group consisting of methylene chloride, chloroform, methyl ethyl ketone, ethyl acetate, butanol or a mixture of these.

8. The process according to claim 1 wherein the dry granulation is performed at a temperature of no more than 40°–50° C.

9. The process according to claim 1 wherein the dry granulation is performed by compressing between rollers under a pressure of 30–90 bar.

10. The process according to claim 1 wherein the dry granulated tetrahydrate is mixed with a filling agent selected from the group consisting of lactose, microcrystalline cellulose, starch or its derivative, mannitol, glucose, saccharose or a mixture of two or more filling agents.

11. The process according to claim 10 wherein the amount of filling agent is about 0–20% by weight of the preparation.

12. The process according to claim 1 wherein the dry granulated tetrahydrate is mixed with a gliding agent selected from the group consisting of calcium stearate, magnesium stearate, talc, starch, colloidal silica or a mixture of two or more gliding agents.

13. The process according to claim 12 wherein the amount of gliding agent is about 0–10% by weight of the final preparation.

14. The process according to claim 1 wherein the granulated tetrahydrate is mixed with a disintegrant selected from the group of sodium carboxymethylcellulose, starch or its derivative, croscarmellose, crospovidone or a mixture of two or more disintegrants.

15. The process according to claim 14 wherein the amount of disintegrant is about 0–3% by weight of the final preparation.

16. The process according to claim 1 wherein the resulting dry granulated disodium clodronate tetrahydrate is further processed to a drug delivery form, which contains 60–80% by weight of the final preparation.

17. The process according to claim 16 wherein a capsule of the preparation is prepared, which comprises 65–75% by weight of disodium clodronate tetrahydrate, calculated in anhydrous form, about 2–12% by weight of a filling agent about 2–6% by weight of a gliding agent and about 0–1% by eight of a disintegrant, based on the weight of the final preparation.

18. A pharmaceutical preparation obtained according to the process of claim 1.

* * * * *